United States Patent [19]
Wood

[11] Patent Number: 5,787,895
[45] Date of Patent: *Aug. 4, 1998

[54] KISSING SHIELD AND METHOD OF USE THEREOF

[76] Inventor: Deloris Gray Wood. R.R. 5. Box 134, Salem. Mo. 65560

[*] Notice: The term of this patent shall not extend beyond the expiration date of Pat. No. 5,534,620.

[21] Appl. No.: 851,871

[22] Filed: May 6, 1997

Related U.S. Application Data

[63] Continuation of Ser. No. 451,652, May 26, 1995, Pat. No. 5,727,565, which is a continuation of Ser. No. 980,354, Nov. 23, 1992, abandoned, which is a continuation-in-part of Ser. No. 776,196, Oct. 15, 1991, abandoned, which is a continuation-in-part of Ser. No. 589,371, Sep. 28, 1990, abandoned.

[51] Int. Cl.$^6$ ............................................. A61F 11/00
[52] U.S. Cl. ................................ 128/857; 128/859
[58] Field of Search ............................ 128/846, 859, 128/860–862, 857; 2/9, 174, 21

[56] References Cited

U.S. PATENT DOCUMENTS

| | | | |
|---|---|---|---|
| D. 210,183 | 2/1968 | Ross | D86/10 |
| D. 225,910 | 1/1973 | Kurianski | D86/10 |
| 566,730 | 8/1896 | McCullen | |
| 1,166,977 | 1/1916 | Favary | |
| 1,199,529 | 9/1916 | Collman | |
| 1,365,684 | 1/1921 | Guise | |
| 1,480,780 | 1/1924 | Pauley | |
| 1,597,806 | 8/1926 | Kvare | |
| 2,123,343 | 7/1938 | Rightsell | 2/21 |
| 2,149,067 | 2/1939 | Otero | 128/139 |
| 2,203,562 | 6/1940 | Edwards | 2/206 |
| 2,265,529 | 12/1941 | Kemp | 128/139 |
| 2,804,123 | 8/1957 | Kling | 155/69 |
| 3,180,639 | 4/1965 | Cotler et al. | 272/1 |
| 3,428,978 | 2/1969 | Johnson | 9/11 |
| 3,477,074 | 11/1969 | Bezanis | 9/11 |
| 3,695,565 | 10/1972 | Hodges | 248/97 |
| 3,729,847 | 5/1973 | Chandos | 40/125 |
| 3,740,768 | 6/1973 | McCosker | 2/174 |
| 3,771,247 | 11/1973 | De Harak | 40/152 |
| 3,772,707 | 11/1973 | Alosi et al. | 2/174 |
| 3,781,994 | 1/1974 | Hesselgren | 32/35 |
| 3,802,429 | 4/1974 | Bird | 128/146.2 |
| 4,034,495 | 7/1977 | Lemelson | 40/137 |
| 4,050,457 | 9/1977 | Davidson | 128/145.5 |
| 4,084,585 | 4/1978 | Venaleck | 128/146.2 |
| 4,486,975 | 12/1984 | Harreld et al. | 446/220 |
| 4,498,652 | 2/1985 | Malik | 248/99 |
| 4,583,946 | 4/1986 | Shanel | 433/136 |
| 4,664,628 | 5/1987 | Totaro | 433/136 |
| 4,781,709 | 11/1988 | Grubman | 604/349 |
| 4,815,456 | 3/1989 | Rubin et al. | 128/859 |
| 4,825,878 | 5/1989 | Kuntz et al. | 128/857 |
| 4,837,861 | 6/1989 | Cole | 2/9 |
| 4,856,535 | 8/1989 | Forbes | 128/857 |
| 4,872,465 | 10/1989 | Kuntz et al. | 128/857 |
| 4,944,312 | 7/1990 | Smith | 128/857 |
| 4,974,605 | 12/1990 | Esqueda | 128/857 |
| 5,112,322 | 5/1992 | Hathaway | 604/317 |

FOREIGN PATENT DOCUMENTS

| | | |
|---|---|---|
| 3920996 | 5/1990 | Germany . |
| 948667 | 2/1964 | United Kingdom . |
| 1061321 | 3/1967 | United Kingdom . |
| 2039406 | 8/1980 | United Kingdom . |

*Primary Examiner*—Michael A. Brown
*Attorney, Agent, or Firm*—Dunlap & Codding, P.C.

[57] ABSTRACT

A kissing shield comprised of a thin, flexible membrane and a frame or holder. The membrane is closed on three sides, a fourth side remaining open so that the membrane can be stretched over the frame or holder. The frame or holder consists of a supporting member and an elongated handle. The supporting member adapts over the bottom part of the user's face and has sufficient dimension to cover the lips and most of the cheeks and extends from under the nose to the bottom of the chin. The elongated handle extends laterally from the supporting member and is sized to be held in the hand of the user such that the hand is spaced apart from the supporting member and membrane.

In use, the membrane is placed over the frame or holder. Using the handle portion of the frame or holder, the user places the kissing shield under his nose, so that it covers his lips, cheeks and chin. The user then positions the kissing shield between his lips and the lips or cheek of the individual he plans to kiss and kisses the intended recipient of his affection.

24 Claims, 4 Drawing Sheets

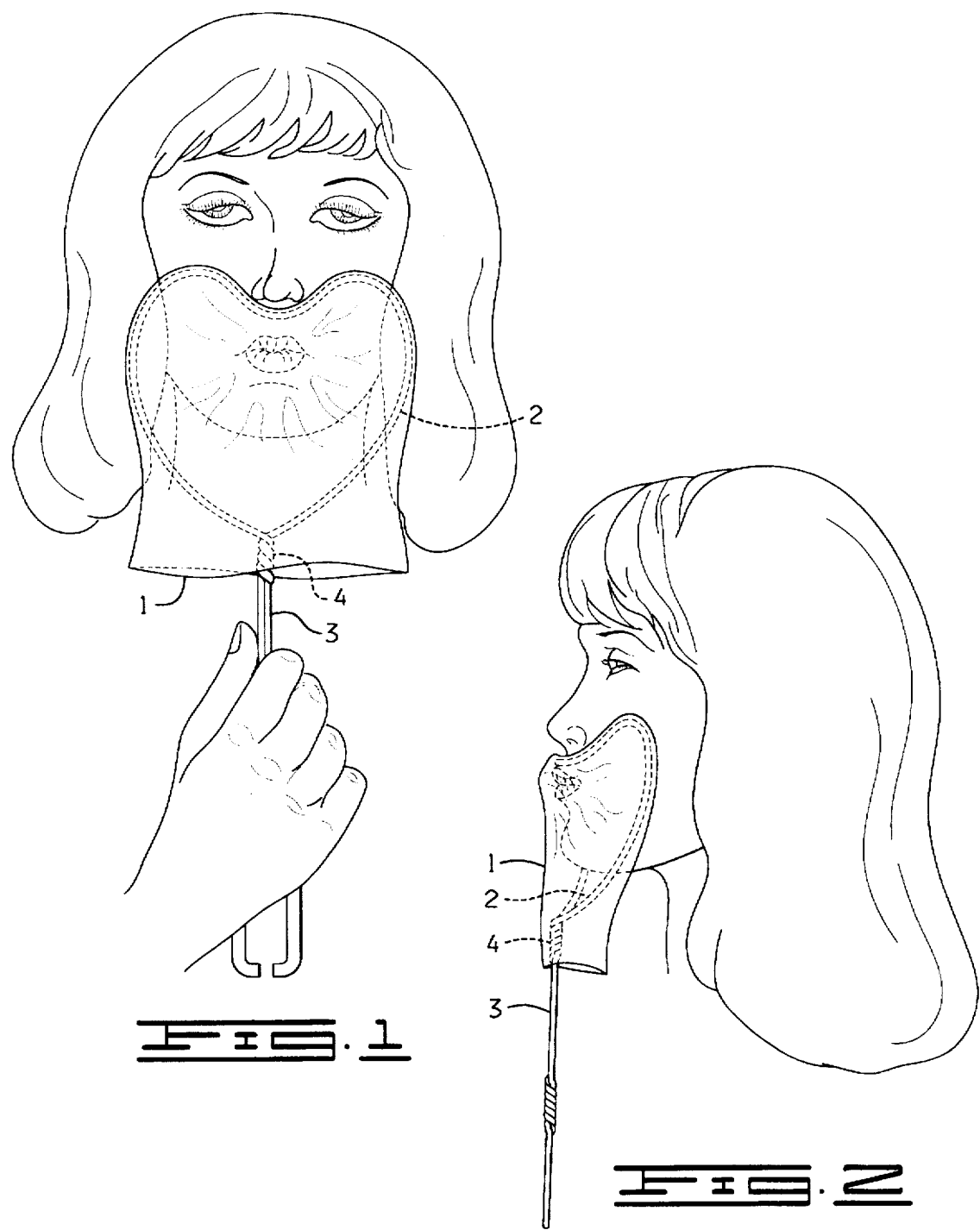

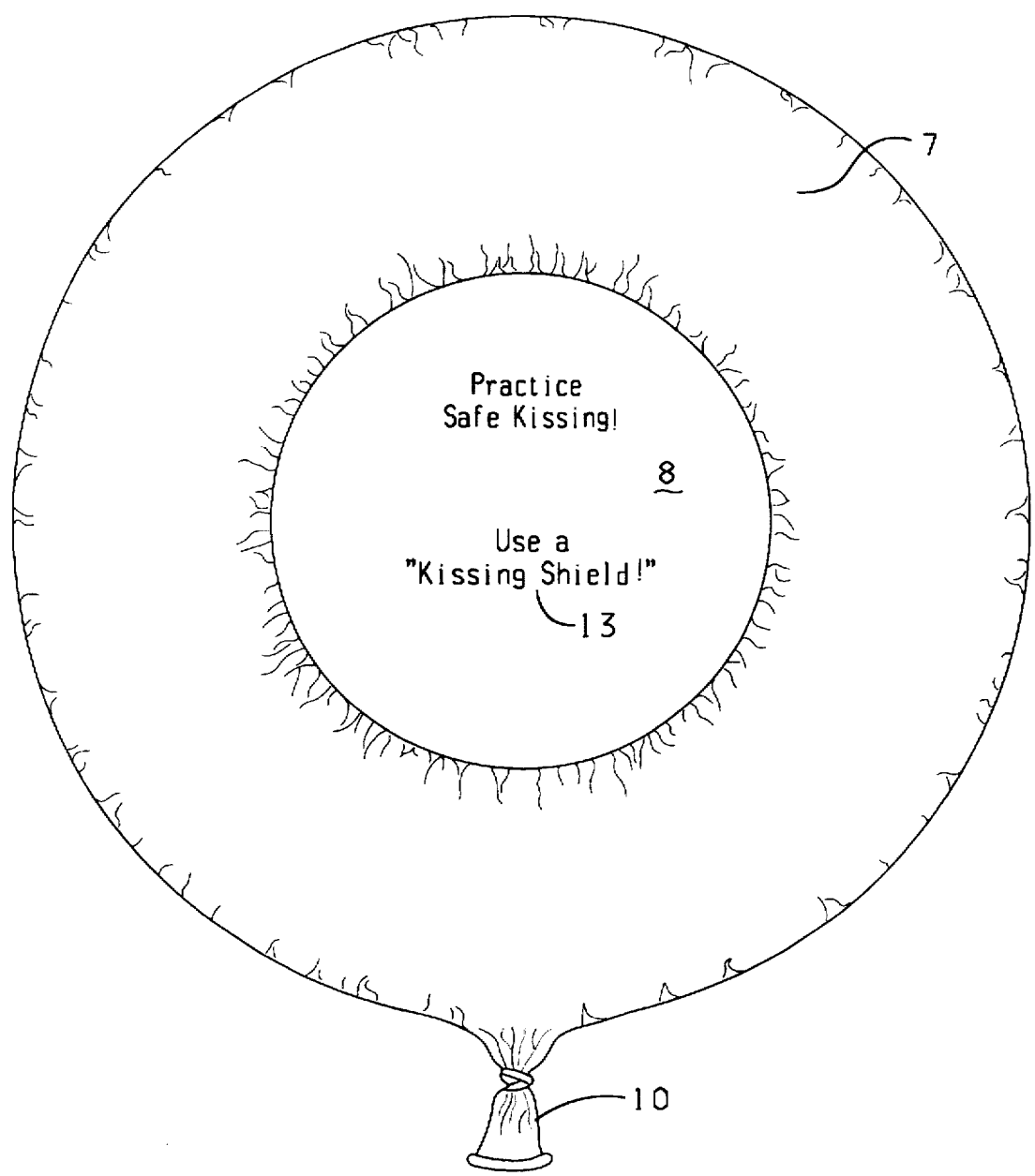

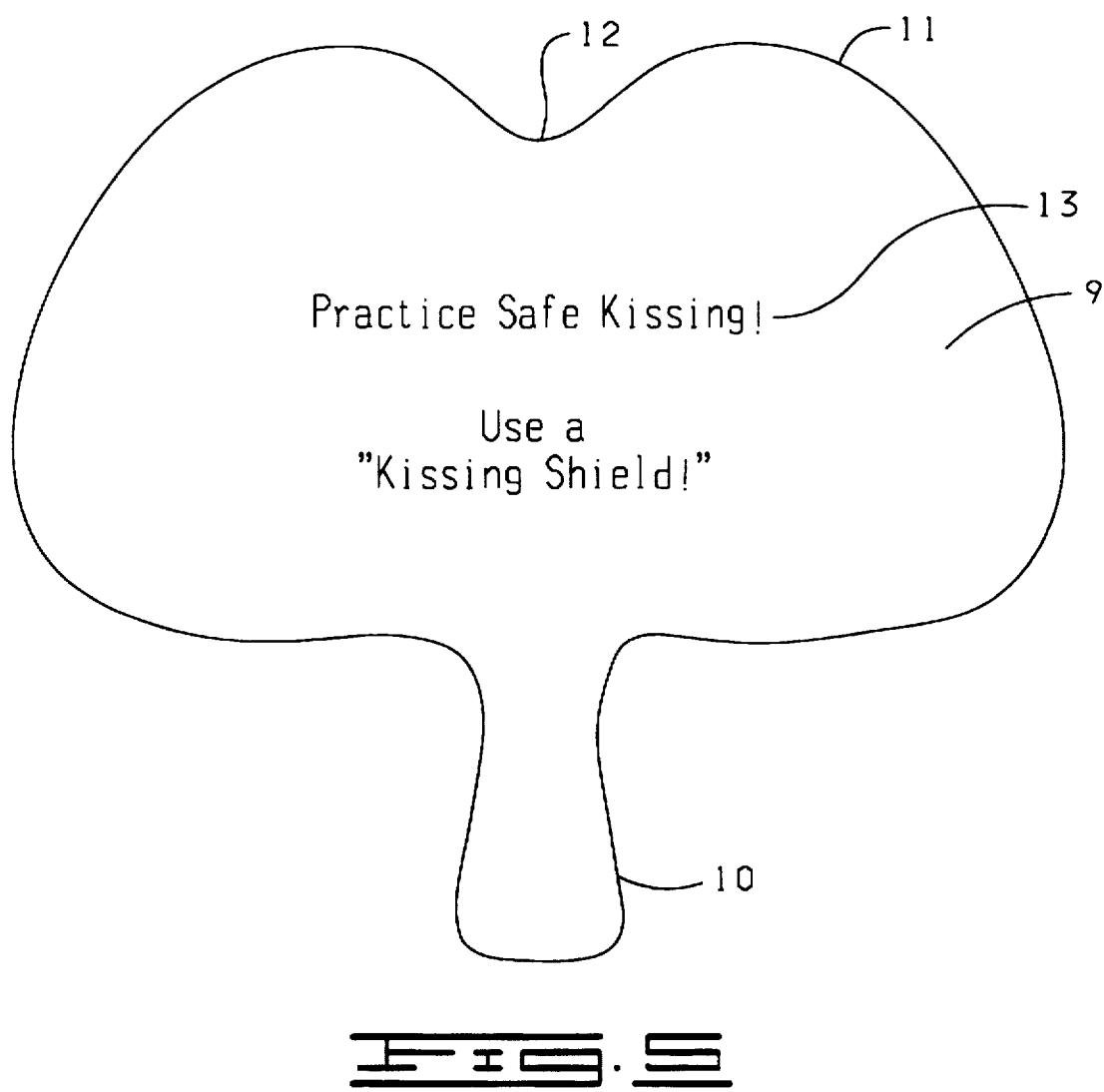

KISSING SHIELD AND METHOD OF USE THEREOF

This application is a continuation of U.S. application Ser. No. 08/451,652, filed May 26, 1995, now U.S. Pat. No. 5,727,565, which is a continuation of U.S. Ser. No. 07/980,354, filed Nov. 23, 1992, now abandoned, which is a continuation-in-part of U.S. Ser. No. 07/776,196, filed Oct. 15, 1991, now abandoned, which is a continuation-in-part of U.S. Ser. No. 589,371, filed Sep. 28, 1990, now abandoned.

FIELD OF THE INVENTION

The present invention relates to face shields used for protection of the lips, tongue, mouth, chin, and cheeks from exposure to germs and diseases, in general, and in particular, to face shields which can be used while engaging in the act of kissing another person.

BACKGROUND OF THE INVENTION

There is a growing awareness of the seriousness of diseases, like Acquired Immunodeficiency Syndrome (AIDS), being spread and the need for protection of those not exposed to such diseases. At times, there has been hysteria among parents and other students, who are afraid their children or they themselves will become infected from classroom and playground contact, when students with AIDS or the Human Immunodeficiency Virus (HIV) have attended school. Also, persons who carry the herpes virus sometimes have lip sores which are usually not distinguishable from an ordinary canker sore or a fever blister by a lay person.

It is customary when we kiss to come in contact with another's lips, and in certain cultures, to follow with a kiss on the skin of each cheek; thus germs can be passed from one person to another. In keeping with one aspect of the invention, if casual contact is necessary and a kiss is appropriate, one can protect oneself from the germs present in saliva or other secretions which might be transmitted from kissing by using a kissing shield.

The present invention proposes a method and device in which a flexible membrane is used as a kissing shield to lessen one's chances of becoming infected by disease from casual contact. In the alternative, if a person is infected, the chances of transferring the infectious disease from one person to another could be reduced by use of a thin, resilient, flexible, impervious membrane, preferably selected from the class of polyethylene, vinyl, and polypropylene materials, stretched over a frame or holder. This would lessen the spread of bodily fluids from one person to another when kissing with the end result of preventing the spread of viruses and diseases, such as canker sores, fever blisters, and AIDS, until there is a cure and prevention of the diseases. The advantages of a kissing shield over regular kissing will become apparent on consideration of the following specification and the accompanying drawings wherein there is disclosed a preferred embodiment.

The kissing shield has both social and health benefits, if basic precautions, such as those one would engage in while using a condom to practice "safe sex", or as a dentist would use when he dons rubber gloves to prevent bodily fluids, such as blood and saliva from his patient, from spreading to his hands and thereby infecting him, are used. The kissing shield can be economically mass produced so that it could be easily disposed of after kissing a person and replaced with a new one.

The kissing shield is for people who desire to be cautious when in contact with another person as they kiss. Use of the kissing shield is convenient and practical. However, like most items we use when we must alter our habits, education is an important step. The kiss is one of the first forms of affection that we display to another. It seems only natural that we would start at a fundamental level and teach "safe kissing" before we teach "safe sex".

The kissing shield, if handled properly, will help people who want to do whatever they can while kissing to practice "preventive medicine" and ensure that disease is not passed from one person to another by proper sanitation or cleanliness of one or both parties. A person who might have a disease and a person who does not want to get the disease or a person who is being protected would take precautionary moves to help prevent the spread of diseases, such as AIDS, by first practicing "safe kissing".

A kissing shield is for casual kissing. It can be used especially by a politician who kisses babies.

It is therefore a primary object of the invention to provide a simple, inexpensive kissing shield to be used when kissing mouth-to-mouth or mouth-to-cheek thereby avoiding the necessity for skin contact with the person to whom affection is intended. It is another object of the invention to provide a means for removing the hesitancy a user may have in kissing another individual without sacrificing the effectiveness of the kiss. It is a further object of the invention to provide a means of preventing the transmission of germs or viruses from saliva or other secretions and the transfer of lipstick or other cosmetics when individuals are engaged in kissing. It is another object of the invention to provide a shield which does not need to be worn. It is a final object of the invention to provide a shield which is economical in construction, such that the device can be used once and thereafter disposed of. Other objects and features will be in part apparent and in part pointed out hereinafter.

SUMMARY OF THE INVENTION

The present invention consists of a shield, which is formed of a thin, flexible, impervious membrane, and a frame or holder. In one embodiment, the membrane consists of two plies closed on three sides and open on the fourth side so as to create a bag which can be stretched over a frame or holder. The kissing shield frame or holder adapts over the bottom part of the user's face and has a handle which extends laterally from the shield and is sized to be held by the user. It has sufficient dimension to cover the lips and most of the cheeks and extends from under the nose to the bottom of the chin. The shield compresses when two sets of lips meet in a kiss or when one set of lips meets the cheek. When compressed, the thin membrane facilitates the tactile sensation of kissing while maintaining the impervious membrane to prevent the spread of germs. The handle of the frame projects a sufficient distance from the membrane so that the hand holding the frame does not interfere with contact between the kissing parties. The present invention thus helps prevent the spread of germs and viruses that can be spread from the saliva and other secretions of one person to another while kissing.

In use, the membrane is placed over the frame or holder. While grasping the handle portion of the frame or holder at a location spaced apart from the thin, flexible membrane, the user places the kissing shield under his nose, so that it covers his lips, cheeks and chin. The user then positions the kissing shield between his lips and the lips or cheek of the individual he plans to kiss and kisses the intended recipient of his affection.

In other embodiments of the present invention, the kissing shield might be a balloon shaped frame with a center web or a bag with an elongated, protrusion for use with the tongue. The device might also be sized for use as a toy by a child.

BRIEF DESCRIPTION OF THE DRAWINGS

FIG. 1 shows a plan view of the present invention with a kissing shield placed over the frame or holder and held in position for use.

FIG. 2 is a side view of the present invention shown in FIG. 1.

FIG. 4 shows a balloon shaped kissing shield having a center web with indicia to inform the user.

FIG. 5 shows a toy kissing shield.

DETAILED DESCRIPTION OF THE DRAWINGS

Figure 3:
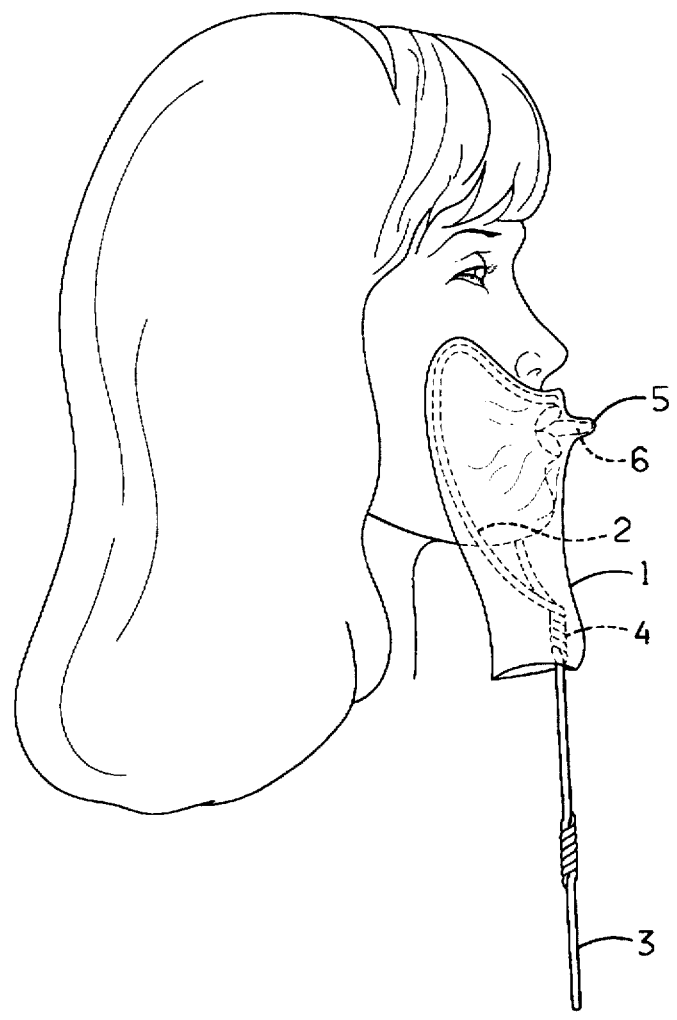
FIG. 3 is a side view of an embodiment of the present invention in which the kissing shield has a protuberance for the tongue.

Referring now to the drawings wherein like reference characters represent like elements, FIG. 1 shows a thin, flexible, impervious membrane 1 placed over a holder 2 and positioned in the appropriate location for use. Membrane 1 is closed on three sides; a fourth side remains open so that the shield may be placed over frame 2. Membrane 1 may be selected from the group of thin, flexible, impervious materials, such as polyethylene, vinyl, and polypropylene. Holder 2 is comprised of a handle 3 and crook 4. Crook 4 is cordate so that it can be placed under the nose of the user while protecting the cheeks, lips, and chin of the user. Handle 3 extends laterally from crook 4 and is sized so that when the user grasps the device, his hand will be located at a distance from the membrane. It will be appreciated that membrane 1/holder 2 can be sized to be employed by a variety of users. As shown in FIG. 2, crook 4 is adapted to surround the lower part of the face of the user.

FIG. 3 shows thin, flexible, impervious membrane 1 having a protuberance 5 located near the uppermost portion of membrane 1. Protuberance 5 creates a space 6 into which the tongue of a user may be placed for a particular type of kissing.

FIG. 4 shows a balloon shaped embodiment of the present invention. In this particular embodiment, a membrane 8 is located within a donut-shaped, circular frame 7. As illustrated, a message could be located within membrane 8 for the purpose of informing the user of the proper side of the device to place against his face, among other things. It would be desirable to have the message printed on the inside of a clear membrane so as to prevent the lips from kissing the printed message.

FIG. 5 shows a flexible, plastic sheet 9 suitable for use by a child. Sheet 9 is shaped to include a handle 10, a flexure 11 to cover the cheeks of the child, and a depression 12 suitable for placement under the nose of the user. A message 13 is centered on sheet 9. Handle 10 extends laterally from flexure 11 and is sized so that when the device is used, the hand of the user will be spaced apart from flexure 11.

It should be noted that the foregoing drawings and accompanying descriptions are intended to be exemplary of several preferred embodiments of the invention and are not exhaustive of the possibilities of the types of shields within the intended scope of the invention. It should also be understood that modifications will readily occur to those skilled in the art within the spirit of the invention. Such modifications could include using different color materials on each side of the membrane or sheet to ensure that the user consistently originates his kisses from the same side of the membrane.

The frame or holder onto which the thin, flexible, impervious membrane is placed could be made of a plastic material, such as nylon, so that it could be sanitized for use by different people. The frame or holder might also be made of a firm, yet flexible material which would allow the device to be adjusted or shaped by the user for individual faces. The membrane could also be made of a plastic material which would be unaffected by products, such as foundation, lipstick, petroleum jelly, and other cosmetics routinely used by most women.

In view of the above, it will be seen that the several objects of the invention are achieved and that other advantageous results are attained. As various changes could be made in the above product and method without departing from the scope of the invention, it is intended that all matter contained in the above description or shown in the accompanying drawings shall be interpreted as illustrative and not in a limiting sense.

What is claimed is:

1. A method for preventing the exchange of microorganisms between a first and a second person who are engaged in the act of kissing, comprising the steps of:

providing a frame so dimensioned as to outline the mouth of at least one of the first person and the second person wherein the frame has a substantially thin and flexible membrane carried by the frame, wherein the membrane is substantially impervious to microorganisms, and wherein the frame includes a handle extending from the frame, with the handle being adapted so that at least one of the first person and the second person is capable of gripping the handle in order to support the frame and membrane supported thereon; and placing the frame so as to outline the mouth of at least one of the first person and second person prior to engaging in the act of kissing, wherein the membrane prevents the exchange of microorganisms between the first person and the second person while engaged in the act of kissing.

2. The method of claim 1, wherein in the step of providing a frame, the membrane is comprised of a material selected from the group consisting of polyethylene, vinyl, polypropylene, and combinations thereof.

3. The method of claim 1, wherein in the step of providing a frame, the frame comprises a loop of material formed into a heart shape having a pair of lobes, wherein each lobe of the heart shape outlines a corresponding cheek area of at least one of the first person and second person such that when the nose of at least one of the first person and second person is positioned between the lobes of the heart shape, the point of the heart shape extends below the chin of at least one of the first person and second person.

4. The method of claim 3, wherein in the step of providing a frame, the frame extends substantially angularly from the handle.

5. The method of claim 3, wherein in the step of providing a frame, the frame extends substantially angularly from the handle and wherein the handle is further substantially collinear with the nose of the person when the frame is positioned to outline the mouth, cheek and chin areas of at least one of the first person and second person.

6. The method of claim 1, wherein in the step of providing a frame, the membrane is removably connected to the frame.

7. The method of claim 1, wherein in the step of providing a frame, the membrane further includes a pocket sized and shaped to receive the tongue of at least one of the first person and second person.

8. The method of claim 1 wherein in the step of providing a frame, the membrane is substantially impervious to a human immuno-deficiency virus.

9. A method for preventing the exchange of microorganisms between a first and a second person who are engaged in the act of kissing, comprising the steps of:

providing a frame so dimensioned as to outline a mouth, a cheek area, and a chin area of at least one of the first person and second person, wherein the frame further includes:

a handle connected to the frame so as to point one of the first and second persons to grip the handle and thereby support the frame and sleeve between the mouth, cheek and chin areas of the first person and the second person, a sleeve supported by the frame, wherein the sleeve is constructed of a substantially thin and flexible sheet of material which is substantially impervious to microorganisms, the sleeve substantially prevents the exchange of microorganisms between the first person and the second person while engaged in the act of kissing; and placing the frame so as to outline the mouth of at least one of the first person and second person prior to engaging in the act of kissing, wherein the membrane prevents the exchange of microorganisms between the first person and the second person while engaged in the act of kissing.

10. The method of claim 9, wherein in the step of supporting a sleeve, the sleeve is comprised of a material selected from the group consisting of polyethylene, vinyl, polypropylene, and combinations thereof.

11. The method of claim 10, wherein in the step of supporting a sleeve, the sleeve is removably connected to the frame.

12. The method of claim 9, wherein in the step of providing a frame, the frame comprises a loop of material substantially formed into a heart shape such that each lobe of the heart shape outlines a corresponding cheek area of at least one of the first person and second person, the nose of at least one of the first person and second person is positioned substantially between the lobes of the heart shape, and the point of the heart shape extends below the chin of at least one of the first person and second person.

13. The method of claim 12, wherein in the step of providing a frame, the frame extends substantially angularly from the handle.

14. The method of claim 12, wherein in the step of providing a frame, the frame extends substantially angularly from the handle such that the handle is substantially collinear with the nose when the frame is positioned to outline the mouth, cheek and chin areas of at least one of the first person and second person.

15. The method of claim 9, wherein in the step of supporting a sleeve, the sleeve further includes a pocket sized and shaped to receive the tongue of at least one of the first person and second person.

16. The method of claim 9, wherein in the step of supporting a sleeve, the sleeve is substantially impervious to a human immunodeficiency virus.

17. The method of claim 9, wherein in the step of supporting a sleeve, the sleeve is a bag, an open end operably positioned so as to slide onto the frame, wherein the frame supports the bag so that the sleeve comprises a material having a double thickness.

18. A method for preventing the exchange of microorganisms between a first and a second person who are engaged in the act of French kissing, comprising the steps of:

providing a loop frame so dimensioned as to outline a mouth, a cheek area, and a chin area of at least one of the first person and second person, wherein the frame further includes:

a handle connected to the frame so as to permit one of the first and second persons to grip the handle and thereby support the frame and membrane between the mouth, cheek and chin area of the first person and second person, a sleeve supported by the frame, wherein the sleeve is constructed of a substantially thin and flexible sheet of material which is further substantially impervious to microorganisms, wherein the sleeve further includes a protuberance defining a space sized and shaped to receive the tongue of at least one of the first person and second person, wherein the sleeve prevents the exchange of microorganisms between the first person and second person while engaged in the act of French kissing; and placing the frame so as to outline the mouth of at least one of the first person and second person prior to engaging in the act of kissing, wherein the membrane prevents the exchange of microorganisms between the first person and the second person while engaged in the act of kissing.

19. The method of claim 18, wherein in the step of providing a frame, the frame comprises a loop of material substantially formed into a heart shape such that each lobe of the heart shape outlines a corresponding cheek area of at least one of the first person and the second person, the nose of at least one of the first and second person is positioned substantially between the lobes of the heart shape, and the point of the heart shape extends below the chin of at least one of the first and second person.

20. The method of claim 18, wherein in the step of providing a frame, the frame extends substantially angularly from the handle.

21. The method of claim 18, wherein in the step of providing a frame, the frame extends substantially angularly from the handle such that the handle is substantially collinear with the nose when the frame is positioned to outline the mouth, cheek and chin areas of at least one of at least one of the first person and the second person.

22. The method of claim 18, wherein in the step of supporting a sleeve, the sleeve is removably connected to the frame.

23. The method of claim 18, wherein in the step of supporting a sleeve, the sleeve is substantially impervious to a human immunodeficiency virus.

24. The method of claim 18, wherein in the step of supporting a sleeve, the sleeve is a bag, wherein the bag has an open end operably positioned so as to slide onto the frame, wherein the frame supports the bag so that the sleeve comprises a material having a double thickness.

* * * * *

UNITED STATES PATENT AND TRADEMARK OFFICE
CERTIFICATE OF CORRECTION

PATENT NO. : 5,787,895

DATED : August 4, 1998

INVENTOR(S) : Wood

It is certified that error appears in the above-identified patent and that said Letters Patent is hereby corrected as shown below:

```
Cover page, [*] Notice, delete "Pat. No. 5,534,620"
and substitute therefor --Pat. No. 5,727,565--.
```

Signed and Sealed this

Fifth Day of January, 1999

Attest:

Attesting Officer

*Acting Commissioner of Patents and Trademarks*